United States Patent [19]

Goel

[11] Patent Number: 4,826,960

[45] Date of Patent: May 2, 1989

[54] NOVEL REACTIONS OF BICYCLIC AMIDE ACETALS WITH REACTIVE PROTIC COMPOUNDS HAVING THE FORMULA HN(R')YR²

[75] Inventor: Anil B. Goel, Worthington, Ohio

[73] Assignee: Ashland Oil, Inc., Ashland, Ky.

[21] Appl. No.: 850,656

[22] Filed: Apr. 11, 1986

[51] Int. Cl.⁴ .............. C07C 113/00; C07C 103/127; C07C 103/22; C07C 125/00

[52] U.S. Cl. .................................. 534/591; 534/588; 534/886; 548/231; 548/257; 548/300; 548/305; 548/306; 548/543; 560/159; 564/93; 564/94; 564/106; 564/184; 564/224

[58] Field of Search ...................... 534/588, 591, 886; 548/231, 257, 306, 543, 300, 305; 560/159; 564/93, 94, 106, 184, 224

[56] References Cited

PUBLICATIONS

Fineauer, Chemical Abstracts, vol. 66, 947864 (1967).

*Primary Examiner*—Floyd D. Higel
*Attorney, Agent, or Firm*—John F. Jones

[57] ABSTRACT

The process for the reaction of bicyclic amide acetals with reactive protic compounds of the general Formula

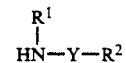

wherein Y represents a member selected from the group consisting of

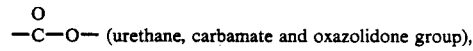

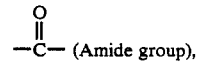

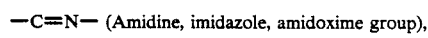

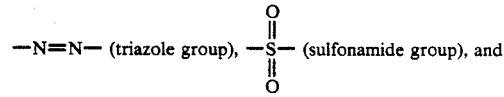

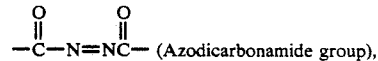

$R^1$ represents a member selected from the group consisting of hydrogen, an alkyl group having from 1 to 10 carbon atoms, an aryl group having from 6 to 12 carbon atoms, and $R^2$ represents a member selected from the group consisting of an alkyl group having from 1 to 10 carbon atoms, an aryl group having from 6 to 12 carbon atoms, an alkylene ether group having from 1 to 50 carbon atoms, an arylene ether group having from 6 to 50 carbon atoms such as ethyl carbamate to form novel products which are useful as curing agents, blowing agents and monomers is disclosed.

15 Claims, No Drawings

NOVEL REACTIONS OF BICYCLIC AMIDE ACETALS WITH REACTIVE PROTIC COMPOUNDS HAVING THE FORMULA HN(R')YR²

This invention relates to a process for the reaction of bicyclic amide acetals with certain organic protic compounds and to the novel products of this process which can be either final products or intermediate products for use in the formation of more complex products.

I have discovered that bicyclic amide acetals will undergo reaction with a variety of reactive protic compounds of general Formula I

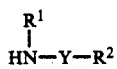     I wherein Y represents a member selected from the group consisting of

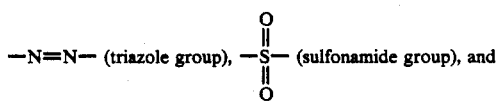

$R^1$ represents a member selected from the group consisting of hydrogen, an alkyl group having from 1 to 10 carbon atoms, an aryl group having from 6 to 12 carbon atoms, and $R^2$ represents a member selected from the group consisting of an alkyl group having from 1 to 10 carbon atoms, an aryl group having from 6 to 12 carbon atoms, an alkylene ether group having from 1 to 50 carbon atoms and an arylene ether group having from 6 to 50 carbon atoms, to give novel ring opening products which can be intermediate or final products. The preparation of bicyclic amide acetals and some of their reactions are more fully described in W. German Patent Publication No. 2,344,607 and in *Synthesis*, 16–26 (1971).

The reaction of bicyclic amide acetals with the reactive protic compounds of this invention has not previously been disclosed.

The novel products of the process of this invention may be used as curing agents, blowing agents, and monomers in different polymerization reactions in which more valuable and useful products are produced.

I have discovered that mono-, bis- or poly-bicyclic amide acetals having one or more groups of Formula II

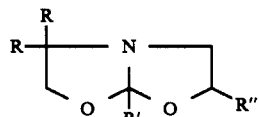     II wherein R, R', and R" independently represent a member selected from the group consisting of hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms and an aryl ether group having from 6 to 20 carbon atoms will react with a variety of compounds having a nitrogen atom with reactive protons thereon as more fully described above.

The process of this invention is usually exothermic and will take place at from about room temperature up to about 200° C. or higher but it is preferred that it be carried out at a temperature in the range of from about 70 to 130 degrees C. The amount of amide acetal to the reactive protic molecules preferred is about one equivalent per equivalent of the protic molecule, however, lower amounts of amide acetal may be used where only partial reaction is desired.

It is believed that the initial reaction of the bicyclic amide acetal with the compound having reactive groups of general Formula I proceeds via ring opening of the amide acetal to give the corresponding product with an hydroxy alkyl amide group as shown in the following reaction

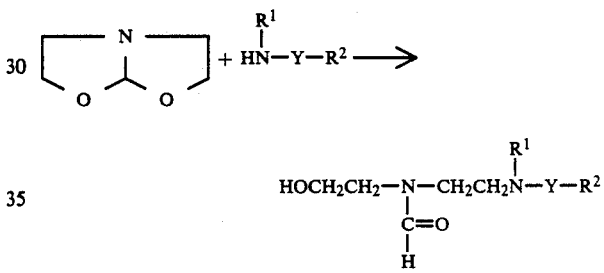

wherein Y, $R^1$ and $R^2$ have the foregoing designations. The resulting product (or intermediate) may also undergo further reaction to produce a polymeric (oligomeric) product.

The process and products of this invention are further illustrated in the following representative examples.

EXAMPLE 1

A 100 ml reactor equipped with a mechanical stirrer, a thermometer with temperature controller, a Dean Stark type receiver with a water condenser, and nitrogen gas inlet, was charged with 17.8g of ethyl carbamate and 26g of a bicyclic amide acetal of Formula II wherein R and R" represent hydrogen and R' represent a methyl group. The resulting mixture was heated to about 100 degrees C. under nitrogen with constant stirring. An exothermic reaction occurred at about 100° C. and the reaction temperature suddenly rose to 120 degrees C. The reaction temperature was then maintained at 120–140 degrees C. for four hours during which time about 6g of ethanol was collected in the Dean Stark tube. The resulting viscous liquid which turned to a highly viscous paste product when cooled to room temperature was analyzed by GLC and showed complete disappearance of the starting bicyclic amide acetal. The infrared spectrum for the product showed the presence of bands at 3350 cm$^{-1}$ (hydroxy group), 1620 cm$^{-1}$ (amide group) in addition to urethane group band at 1650–1720 cm$^{-1}$. A weak-to-medium band at 2150 cm$^{-1}$ was also observed and was probably caused by the presence of a carbodiimide group.

EXAMPLE 2

A mixture 17.4g of oxazolidone and 26g of the bicyclic amide acetal of Example 1 was heated at 150 degrees with stirring for 3 hours in the manner described in Example 1. The resulting viscous liquid was analyzed by GLC which showed that virtually all of the starting bicyclic amide acetal had been consumed in the process. The infrared spectrum for the product showed the presence of strong bands at 3350 cm$^{-1}$ (hydroxy group) and 1620 cm$^{-1}$ (amide group) in addition to the urethane group band at 1720 cm$^{-1}$, thus showing the formation of the compound having the structure

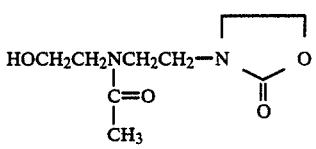

EXAMPLE 3

A mixture of 12.12g of benzamide and 13.1 g of the bicyclic amide acetal described in Example 1 was heated to 140 degrees C. in accordance with the procedure of Example 1. An exothermic reaction occurred at about 135° C. and the temperature suddenly jumped to about 200 degrees C. during the exotherm. Following this the reaction temperature was maintained at 150 degrees C. for two hours and the resulting viscous liquid was analyzed by GLC which showed the complete consumption of the starting bicyclic amide acetal. The infrared spectrum of the product showed the presence of strong bands at 3350 cm$^{-1}$ (hydroxy group) and 1620 cm$^{-1}$ showing the formation of hydroxy alkyl amide by the bicyclic amide acetal ring opening reaction.

EXAMPLE 4

The procedure of Example 1 was followed. The stirred mixture of 12g of acetamide and 26g of bicyclic amide acetal was allowed to react at 160 degrees C. for 8 hours. The resulting viscous liquid showed the presence of strong infrared bands at 3300-3350 cm$^{-1}$ (hydroxy group) and 1620 cm$^{-1}$ indicating the formation of hydroxy alkyl amide groups.

EXAMPLE 5

A mixture of 11.06g of 4,4-dimethyl-2-oxazolidone and 13.03g of the bicyclic amide acetal described in Example 1 was allowed to react at 150 degrees C. for four hours following the procedure of Example 1. The resulting liquid product was analyzed by GLC which showed the consumption of about 55% of the bicyclic amide acetal. This indicates that the substitutions causing steric hinderance result in reducing the reaction rate when compared with that of Example 5. The reaction was continued for another 8 hours at 150 degrees C. and the product when then analyzed showed complete absence of the bicyclic amide acetal by GLC and infrared showed bands at 3350 cm$^{-1}$ (hydroxyl group and 1620 cm$^{-1}$ (amide group).

EXAMPLE 6

In accordance with the procedure of Example 1 a mixture of 17g of pyrrolidone and 26g of the bicyclic amide acetal described in Example 1 was allowed to react at 160 degrees C. for 8 hours. The resulting viscous liquid was analyzed by infrared which showed the formation of bands at 3330 cm$^{-1}$ (hydroxy group) and 1620 cm$^{-1}$ (amide group). The GLC analysis of the product showed the consumption of starting bicyclic amide acetal was about 88% during this reaction time.

EXAMPLE 7

In accordance with the procedure of Example 1 a cloudy mixture of 11.8g of benzimidazole and 13g of the bicyclic amide acetal described in Example 1 was heated at 90 degrees C. with stirring. A clear solution formed and and exotherm began. The reaction temperature jumped to about 145 degrees C. within a few minutes and the solution became viscous. The reaction was continued at 150 degrees C. for 30 minutes and the viscous liquid was analyzed by GLC which showed the complete disappearance of the starting bicyclic amide acetal. The infrared spectrum for the product showed bands at 3200-3350 cm$^{-1}$ (hydroxy group) and 1620 cm$^{-1}$ (amide group).

EXAMPLE 8

Following the general procedure of Example 1 a solution of 11.91g of benzotriazole and 13.02g of the bicyclic amide acetal described in Example 1 was heated at 75 degrees C. and an exotherm took place causing the reaction temperature to jump to 97 degrees C. within three minutes and the resulting highly viscous liquid was analyzed by GLC which showed the complete disappearance of the starting bicyclic amide acetal. The infrared spectrum for the product showed strong bands at 3350 cm$^{-1}$ (hydroxy group and 1620 cm$^{-1}$ (amide group) showing the formation of hydroxy alkyl amide groups.

EXAMPLE 9

In accordance with the procedure of Example 1 a mixture of 17.2g of toluene sulfonamide and 13.2g of the bicyclic amide acetal described in Example 1 was stirred and heated to 60 degrees C. An exothermic reaction occurred and the reaction temperature jumped to 80 degrees C. and all of the starting solid toluene sulfonamide dissolved to give a clear viscous solution. The solution was further heated with stirring at 100 degrees C. for two hours and analysis of the product by GLC showed nearly complete reaction of the starting bicyclic amide acetal. Infrared analysis of the product showed strong bands at 3150-3350 cm$^{-1}$ (OH and NH) and at 1600-1540 cm$^{-1}$ (amide group).

EXAMPLE 10

In accordance with the procedure of Example 1 a mixture of dicyandiamide (8.4g) and 26g of the bicyclic amide acetal described in Example 1 was heated under constant stirring at 140-150 degrees C. for four hours to give a clear viscous solution. Infrared analysis of this material showed bands at 3350 cm$^{-1}$ and 3150-3200 cm$^{-1}$ (OH and NH groups), 2170 cm$^{-1}$ (C=N), 1620 cm$^{-1}$ (amide) and 1560-1600 cm$^{-1}$ (C=C and NH). A part of this product (8g) was mixed with 10g of liquid diglycidyl ether of Bisphenol-A (epoxy equivalent weight of 185-195) and split into two parts. One part was kept at room temperature for four hours and no change was noticed. The other part was heated at 140 degrees C. and gelation occurred within ten minutes to give a solid polymer in 15 minutes. For comparison purposes, no reaction occurred when a mixture of the starting dicyandiamide and the epoxide were allowed to react at 140 degrees C. for more than one hour. This shows that the product of reaction of dicyandiamide with bicyclic amide acetal can be used as an effective latent curing agent for epoxy resins.

EXAMPLE 11

In accordance with the procedure of Example 1 a mixture of 11.62g of azodicarbonamide and 26.1g of the bicyclic amide acetal of Example 1 was allowed to react at 85 degrees C. An exothermic reaction occurred and the reaction temperature jumped to 170 degrees C. with an excessive gas evolution from the reaction mixture. The infrared spectrum of the liquid product showed bands at 3350 cm$^{-1}$ (OH group) and 1620 cm$^{-1}$ (amide group).

Because of the gas evolution observed above, a polyurethane foam was synthesized using a mixture of 6.5g of the bicyclic amide acetal, 2.9g of azodicarbonamide, 0.3g of silicone surfactant (Dow Corning DC 193) and 18g of methylene bis(phenyl isocyanate) (NCO functionality of about 2.3). This mixture was heated to 80 degrees C. An exothermic reaction occurred to give a solid foam polymeric product.

I claim:

1. The process for preparing a product comprising reacting a bicyclic amide acetal having the formula

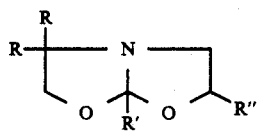

wherein R, R' and R" independently represent a member selected from the group consisting of hydrogen, an alkyl group having from 1 to 20 carbon atoms, an aryl group having from 6 to 12 carbon atoms, an alkaryl group having from 7 to 20 carbon atoms, an alkyl ether group having from 1 to 20 carbon atoms and an aryl ether group having from 6 to 20 carbon atoms, with a reactive protic compound having the formula

wherein Y represents a member selected from the group consisting of

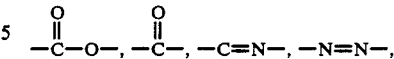
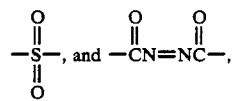

R' represents a member selected from the group consisting of hydrogen, an alkyl group having from 1 to 10 carbon atoms, an aryl group having from 6 to 12 carbon atoms, and R$^2$ represents a member selected from the group consisting of an alkyl group having from 1 to 10 carbon atoms, an aryl group having from 6 to 12 carbon atoms, an alkylene ether group having from 1 to 50 carbon atoms and an arylene ether group having from 6 to 50 carbon atoms, and wherein the process is carried out at a temperature to about 200° C.

2. The process of claim 1 wherein there is present about one equivalent of bicyclic amide acetal per equivalent of the reactive protic compound.

3. The process of claim 2, wherein the bicyclic amide acetal is one in which R and R" represent hydrogen and R' represents a methyl group.

4. The process of claim 3 wherein the reactive protic compound is ethyl carbamate.

5. The process of claim 3 wherein the reactive protic compound is oxazolidone.

6. The process of claim 3 wherein the reactive protic compound is benzamide.

7. The process of claim 3 wherein the reactive protic compound is acetamide.

8. The process of claim 3 wherein the reactive protic compound is 4,4-dimethyl-2-oxazolidone.

9. The process of claim 3 wherein the reactive protic compound is pyrrolidone.

10. The process of claim 3 wherein the reactive protic compound is benzimidazole.

11. The process of claim 4 wherein the reactive protic compound is benzotriazole.

12. The process of claim 3 wherein the reactive protic compound is toluene sulfonamide.

13. The process of claim 3 wherein the reactive protic compound is dicyandiamide.

14. The process of claim 3 wherein the reactive protic compound is azodicarbonamide.

15. The product of the process of claim 1.

* * * * *